United States Patent [19]

Brown

[11] Patent Number: 5,248,493

[45] Date of Patent: Sep. 28, 1993

[54] PHARMACEUTICAL COMPOSITION

[75] Inventor: Kenneth Brown, Loughborough, England

[73] Assignee: Fisons plc, England

[21] Appl. No.: 771,795

[22] Filed: Oct. 4, 1991

Related U.S. Application Data

[63] Continuation of Ser. No. 395,349, Aug. 17, 1989, abandoned.

[30] Foreign Application Priority Data

Aug. 27, 1988 [GB] United Kingdom ............ 88 20398

[51] Int. Cl.$^5$ ..................... A61K 9/12; A61K 31/47
[52] U.S. Cl. ..................... 424/45; 514/291; 514/826
[58] Field of Search .................. 514/291, 826; 424/45

[56] References Cited

U.S. PATENT DOCUMENTS

| | | | |
|---|---|---|---|
| 2,440,915 | 1/1946 | Roehr | 424/45 |
| 3,957,965 | 5/1976 | Hartley et al. | 424/45 |
| 4,356,181 | 10/1982 | Payling et al. | 514/826 |
| 4,581,225 | 4/1986 | Su et al. | 424/45 |
| 4,760,072 | 7/1988 | Brown et al. | 514/291 |
| 4,847,277 | 7/1989 | Gould | 514/382 |
| 4,849,427 | 7/1989 | Nassim et al. | 514/291 |
| 4,851,211 | 7/1989 | Adjei et al. | 424/45 |
| 4,863,720 | 9/1989 | Burghart et al. | 424/45 |
| 4,866,072 | 9/1989 | Edwards et al. | 514/291 |
| 4,918,078 | 4/1990 | Brown et al. | 514/291 |
| 4,935,244 | 6/1990 | Clark | 424/450 |
| 5,198,221 | 3/1993 | Clark et al. | 424/499 |

FOREIGN PATENT DOCUMENTS 0287193 10/1988 European Pat. Off. .
2157291 10/1985 United Kingdom .
2187953 9/1987 United Kingdom .

OTHER PUBLICATIONS

Eur. J. Respir. Dis., vol. 69, Suppl. 147, 1986, pp. 149–159; S. T. Holgate: "Clinical evaluation of nedocromil sodium in asthma."

Aust. New Zealand J. Med., vol. 17, No. 6, 1987; R. E. Ruffin et al., "The efficacy of nedocromil sodium (Tilate) in asthma."

Thorax, vol. 39, Jun. 6, 1984, pp. 809–812; S. Lal et al., "Nedocromil sodium: a new drug for the management of bronchial asthma."

Primary Examiner—Thurman K. Page
Assistant Examiner—Amy Hulina
Attorney, Agent, or Firm—Marshall, O'Toole, Gerstein, Murray & Borun

[57] ABSTRACT

A pharmaceutical composition comprising 9-ethyl-6,9-dihydro-4,6-dioxo-10-propyl-4H-pyrano[3,2-g]quinoline-2,8-dicarboxylic acid or a pharmaceutically acceptable salt thereof, a pressurized or liquefied gas propellant, and a flavoring agent and/or a sweetening agent is useful in the treatment of reversible obstructive airways disease. The composition preferably contains nedocromil sodium as active ingredient. Flavoring agents which may be used include menthol and peppermint oil. Sweetening agents which may be used include sugar, aspartame, cyclamates and saccharin or salts thereof. The composition preferably includes both a flavoring agent and a sweetening agent. Any conventional aerosol propellant may be used, e.g. a mixture of Propellant 12 and Propellant 114, and the composition is preferably packaged in a conventional pressurized aerosol canister fitted with a dispensing metering valve.

6 Claims, No Drawings

PHARMACEUTICAL COMPOSITION

This application is a continuation of application Ser. No. 07/395,349, filed Aug. 17, 1989 and now abandoned.

This invention relates to pharmaceutical formulations, in particular to aerosol formulations for inhalation.

Many drugs, especially those for the treatment of diseases of the respiratory tract, are administered by inhalation. For administration by this route, powdered inhalation drugs are commonly formulated as pressurised aerosols. Nedocromil sodium, the disodium salt of 9-ethyl-6,9-dihydro-4,6-dioxo-10-propyl-4H-pyrano[3,2-g]quinoline-2,8-dicarboxylic acid, is known to be effective in the treatment of inter alia reversible obstructive airways disease when administered by inhalation. Indeed, pressurised aerosol formulations of nedocromil sodium are known, for example from British Patent Application No 2 157 291 A. However, it has been found that certain patients do not derive the full expected therapeutic benefit from the medicament.

We have now found that the incorporation into a pressurised aerosol formulation of nedocromil sodium of a flavouring agent and/or a sweetening agent reduces or substantially overcomes this problem.

Thus, according to the invention there is provided a pharmaceutical composition comprising 9-ethyl-6,9-dihydro-4,6-dioxo-10-propyl-4H-pyrano[3,2-g]quinoline-2,8-dicarboxylic acid or a pharmaceutically acceptable salt thereof, a pressurised or liquefied gas propellant, and a flavouring agent and/or a sweetening agent.

The composition according to the invention is useful in the treatment of reversible obstructive airways disease and is advantageous in that it induces improved patient compliance resulting in more regular use of the medicament with concomitant improvements in the therapeutic benefits to the patient. These effects are especially significant in the case of middle-aged and younger patients whose disease has generally not reached an advanced stage in terms of duration, severity and reversibility.

The composition is also advantageous in that it may have an improved 'dispersion' i.e. may produce a higher proportion of medicament particles which are fine enough to penetrate deep into the lung. In addition, aerosol dispensers containing the compositions of the invention may be less prone to blockage than are containers of known formulations of the active ingredient. Valve action may also be improved by the presence of the flavouring and/or sweetening agents, which may give rise, for example, to reduced leakage and/or greater dose uniformity.

Pharmaceutically acceptable salts of 9-ethyl-6,9-dihydro-4,6-dioxo-10-propyl-4H-pyrano[3,2-g]quinoline-2,8-dicarboxylic acid include the alkali metal salts and the alkaline earth salts. We particularly prefer the disodium salt, which is known by the generic name nedocromil sodium.

A variety of flavouring agents and sweetening agents may be used in the composition according to the invention. For example, suitable flavouring agents include peppermint oil and menthol. The proprietary product known by the tradename Dentomint, which contains both menthol and peppermint oil, may also be used. Suitable sweetening agents include sugar, aspartame, cyclamates and, preferably, saccharin or salts thereof, e.g. saccharin sodium.

We prefer the composition to include both a flavouring agent and a sweetening agent.

We prefer the active ingredient to have a mass median diameter in the range 0.01 to 10 microns, more preferably from 1 to 5 microns. The composition preferably comprises from 0 05 to 15, preferably from 0.1 to 10, and most preferably from 0.5 to 5% w/w active ingredient.

We prefer the flavouring and sweetening agents, when they are solid, to have a mass median diameter in the range 0.01 to 10 microns. The composition preferably comprises up to 5% w/w, more preferably up to 2% w/w, flavouring and sweetening agents.

The pressurised or liquefied gas propellant may be any of the propellants conventionally used in pressurised aerosols. For example, the propellant may be a chlorofluorocarbon such as those known as Propellant 11, Propellant 12 and Propellant 114 or a mixture of two or more thereof. In this case, we prefer the propellant to be a mixture of Propellant 12 and Propellant 114. In particular, we prefer the ratio of Propellant 12 to Propellant 114 to be from about 1:1 to about 2:1, especially about 1.5:1 i.e. we prefer an excess of Propellant 12 over Propellant 114.

Alternatively, the propellant may be a hydrofluorocarbon, e.g. that known as HFC 134a. Other propellants which may be used are compressed gases, e.g. nitrogen and hydrocarbons such as butane.

The composition may also include a surface active agent. The surface active agent may be solid or, more preferably, liquid. The surface active agent is preferably non-ionic. Non-ionic liquid surface active agents which may be mentioned include the oleates of sorbitan. We particularly prefer the surface active agent to be sorbitan trioleate.

The compositions according to the invention preferably contain less than 1.0%, more preferably less than 0.5% and most preferably less than 0.2% w/w of water.

The compositions according to the invention may be prepared by conventional techniques. Generally, all that is required is mixing of the ingredients. Where the propellant is a mixture of Propellant 12 and Propellant 114, the compositions are preferably prepared by mixing the solid components in a pressure vessel, evacuating the vessel and then admitting the propellant mixture.

The compositions according to the invention may be packaged in conventional pressurised aerosol canisters, e.g. aluminium or glass canisters fitted with valves, preferably metering valves, to permit accurate dispensing of aliquots of the composition.

The invention is illustrated, but in no way limited, by the following Examples.

EXAMPLE 1

| Ingredients | % w/w |
| --- | --- |
| Nedocromil sodium (micronised) (calculated as anhydrous material) | 1.442 |
| Sorbitan trioleate | 0.5 |
| Menthol BP | 0.05 |
| Saccharin sodium BP (micronised) | 0.033 |
| Propellant mixture 12/114 (60/40% w/w) | 97.975 |

Method

The sorbitan trioleate, menthol, saccharin sodium (dried and micronised) and nedocromil sodium (micronised) are weighed into a clean, dry batching vessel. The batching vessel is sealed, evacuated and filtered, and the propellant mixture admitted to the required weight.

The mixture is stirred and filled into aluminium aerosol cans fitted with 100 μl metering valves.

EXAMPLE 2

| Ingredients | % w/w |
| --- | --- |
| Nedocromil sodium (micronised) (calculated as anhydrous material) | 1.442 |
| Sorbitan trioleate | 0.5 |
| Dentomint | 0.577 |
| Saccharin sodium BP (micronised) | 0.072 |
| Propellant mixture 12/114 (60/40% w/w) | 97.409 |

Method

Prepared by the method of Example 1.

EXAMPLE 3

| Ingredients | % w/w |
| --- | --- |
| Nedocromil sodium (micronised) (calculated as anhydrous material) | 1.442 |
| Sorbitan trioleate | 0.5 |
| Dentomint | 0.288 |
| Saccharin sodium BP (micronised) | 0.036 |
| Propellant mixture 12/114 (60/40% w/w) | 97.734 |

Method

Prepared by the method of Example 1.

I claim:

1. A method of treatment of reversible obstructive airways disease which comprises administration by inhalation to the lung of a patient suffering from, or susceptible to, that condition a therapeutically effective amount of a pharmaceutical composition comprising particulate 9-ethyl-6,9-dihydro-4,6-dioxo-10-propyl-4H-pyrano[3,2-g]quinoline-2,8-dicarboxylic acid or a pharmaceutically acceptable salt thereof, having a mass median diameter in the range of 0.01 to 10 microns, a pressurized or liquefied gas propellant, and a flavoring agent selected from the group consisting of peppermint oil and menthol.

2. A method of treatment according to claim 1 wherein the pharmaceutically acceptable salt is nedocromil sodium.

3. A method of treatment according to claim 1 wherein the pharmaceutical composition includes a sweetening agent.

4. A method of treatment according to claim 3 wherein the sweetening agent is selected from the group consisting of sugar, aspartame, cyclamates and saccharin or salts thereof.

5. A method of treatment according to claim 1 wherein the propellant is a mixture of Propellant 12 and Propellant 114.

6. A method of treatment according to claim 5 wherein the ratio of Propellant 12 to Propellant 114 is from 1:1 to 2:1.

* * * * *